United States Patent [19]

Jacobson et al.

[11] Patent Number: 4,696,932
[45] Date of Patent: * Sep. 29, 1987

[54] BIOLOGICALLY-ACTIVE XANTHINE DERIVATIVES

[75] Inventors: Kenneth A. Jacobson, Silver Spring, Md.; John W. Daly, Washington, D.C.; Kenneth L. Kirk, Bethesda, Md.

[73] Assignee: The United States of America as represented by the Department of Health and Human Services, Washington, D.C.

[*] Notice: The portion of the term of this patent subsequent to Sep. 16, 2003 has been disclaimed.

[21] Appl. No.: 717,616

[22] Filed: Mar. 29, 1985

Related U.S. Application Data

[63] Continuation-in-part of Ser. No. 664,953, Oct. 26, 1984.

[51] Int. Cl.$^4$ .................. A61K 31/52; C07D 473/06
[52] U.S. Cl. .................................. 514/263; 514/265; 514/17; 514/18; 514/19; 544/269; 544/271; 544/273; 530/330; 530/331; 530/332; 260/998.2
[58] Field of Search ............ 544/269, 271, 273; 514/263, 265, 17, 18, 19; 260/112.5 R, 998.2; 530/330, 331, 332

[56] References Cited

U.S. PATENT DOCUMENTS 4,397,779 8/1983 Groman .................. 260/112.5 R

FOREIGN PATENT DOCUMENTS 92398 10/1918 European Pat. Off. .

OTHER PUBLICATIONS

Bruns, Proc. Natl. Acad. Sci., (USA), 80, pp. 2077–2080 (4/83).

Primary Examiner—Sidney Marantz
Assistant Examiner—Robert Benson
Attorney, Agent, or Firm—John S. Roberts, Jr.

[57] ABSTRACT

Certain functionalized cogeners of 1,3-dialkylxanthine exhibit high potency and selectivity as antagonists for $A_1$- and $A_2$-adenosine receptors and are suitable for attachment to probes, drug carriers, or solid supports. These derivatives are characterized by the presence of a phenyl at the 8 position para-substituted with a functionalized chain to provide high water solubility and high receptor affinity. Some of these analogs, containing a distal amino- or carboxylic-functionalized chain, are suitable for synthesis of amino acid conjugates. The compounds of this invention are suitable for use as antiallergenic, antiasthmatic, or cardiotonic drugs, central nervous system stimulants, and diuretics.

13 Claims, No Drawings

4,696,932

BIOLOGICALLY-ACTIVE XANTHINE DERIVATIVES

This application is a continuation-in-part of Ser. No. 664,953, filed Oct. 26, 1984, now pending.

BACKGROUND

Certain functionalized congeners of 1,3-dialkylxanthine exhibit high potency and selectivity as antagonists for $A_1$- and $A_2$-adenosine receptors and are suitable for attachment to probes, drug carriers, or solid supports. These derivatives are characterized by the presence of a phenyl substituent at the 8 position para-substituted with a functionalized chain to provide high water solubility and high receptor affinity to such an extent that these compounds are suitable for use as antiallergenic, antiasthmatic, or cardiotonic drugs, central nervous system stimulants, and diuretics.

Alkylxanthines, of which theophylline is the most well known, represent a major class of antagonists for adenosine receptors. Although theophylline and other xanthines such as caffeine are relatively weak adenosine antagonists, with affinity constants in the 10–50 micromolar range, they owe many of their pharmacological effects to blockage of adenosine mediated functions at the $A_1$ and $A_2$ receptor sites noted above. The $A_1$-adenosine receptor is inhibitory to adenylate cyclase and appears involved in antilipolytic, cardiac, and central depressant effects of adenosine. The $A_2$-adenosine receptor is stimulatory to adenylate cyclase and is involved in hypotensive, antithrombotic, and endocrine effects of adenosine. Some xanthines, such as 3-isobutyl-1-methylxanthine, not only block adenosine receptors but also have potent inhibitory effects on phosphodiesterases. In an effort to identify highly potent and specific analogs of adenosine receptor antagonists (xanthines) the functionalized "congener approach" was applied, as described in Jacobson et al, *J. Med. Chem.*, 1983, Vol. 26, p. 492. Analogs of adenosine receptor ligands bearing functionalized chains are synthesized and covalently attached to various organic moieties, such as amines and peptides. The binding affinities (competitive CHA binding on rat cerebral cortex) and the specificity are modulated by changes in the attached moiety. The present invention discloses that the presence of a functionalized chain linked to the 8-phenyl group through a —O—CH$_2$CO— linkage greatly enhances the potency of 1,3-dialkylxanthines as adenosine antagonists. Potent antagonists are produced by replacing the 1,3-methyl groups of 8-phenyltheophylline with n-propyl groups and by situating uncharged electron-donating para-substituents on the 8-phenyl ring. Amino acid conjugates are synthesized in which an amino acid "carrier" is linked through an amide bond to a functionalized xanthine congener. In addition to high potency, some of these 1,3-dipropyl-8-phenylxanthine derivatives exhibit selectivity toward either the $A_1$- or $A_2$-subclass of adenosine receptors. The amino congeners, in particular, exhibit improved water solubility and partition characteristics, permitting in vivo use of these congeners.

Many of the xanthines (such as theophylline) exhibit undesirable side-effects, such as cardiac stimulation. The present invention avoids or reduces these side-effects by developing compounds that are more potent or selective adenosine receptor blockers.

Furthermore, the $A_1$-specific antagonists, such as compound 6d, are useful therapeutically in combination with a non-specific adenosine agonist. The net effect of such a combination is decreasing blood pressure (an $A_2$ effect of the agonist) without a concomitant effect on the heart rate (since the $A_1$-agonist effect of slowing the heart rate would be cancelled by the specific antagonist).

In the design of active covalent conjugates of drugs, the goals of the congener approach are several, including targeting, increasing the potency, prolonging the duration of action, and/or changing the specificity, and prodrugs. As noted above, they are useful therapeutically as antiasthmatic and antiallergenic drugs. Non-therapeutic applications of these active functionalized drugs include receptor probes, immobilized ligands for affinity chromatography, and radiolabeled analogs.

A further benefit of applying the congener approach to xanthines is the opportunity to increase water solubility. The series of super-active 8-phenylxanthines [PNAS, Vol. 80, p. 2077 (1983)] is highly non-polar with aqueous solubility very often falling below 10 micromolar, see *Acta Physiol. Scand.*, Vol. 122, pp 191–198 (1984). By increasing water solubility through the attachment of highly polar charged or uncharged groups at positions which are also favorable to potency as adenosine antagonists, it is possible to overcome undesirable binding to plasma proteins and partition into lipids. This leads to improved pharmacokinetics of the drugs.

Some similar known compounds, such as the 8-arylxanthines, contain up to four substituents on the phenyl ring. These substituents usually contribute to the compound's insolubility in water. The present invention not only discloses a single substituent on the phenyl ring, it also discloses a variety of charged and uncharged hydrophilic substituents attached to xanthine through a functionalized chain. The combination of nanomolar potency and water solubility (concentrations approximately 10,000-fold greater than the receptor affinity constants) in the compounds of the present invention indicate high potency plus increased absorption.

GENERAL DESCRIPTION OF THE INVENTION

The present invention discloses the synthesis of a series of highly potent congeners of theophylline and 1,3-dipropylxanthine. Some of these congeners contain groups designed for radiolabeling through introduction of radioisotopes of elements such as iodine, carbon, fluorine, or through metal complexes. The radioisotope is attached by linking the drug to a "radioisotope acceptor" or prosthetic group, which is specially designed for the facile introduction of a particular isotope. These radiolabeled compounds have high adenosine receptor affinities. Those that contain short-lived positron emitters, such as $^{18}F$, are potentially useful for the developmental diagnostic technique of positron emission tomography. Other functionalized congeners of this invention are suitable for the preparation of affinity columns. The amino congeners of 1,3-dipropylxanthine (including those bearing attached chains derived from ethylene diamine) produce affinity constants in the $10^{-9}$ to $10^{-8}$ molar range, favoring high potency as well as improved solubility characteristics.

As noted above, the compounds of this invention are characterized by the presence of lower alkyl groups such as n-propyl groups at the 1 and 3 position on the theophylline ring and by a variety of para-substituents on the 8-phenyl ring. It should be noted, however, that some of the compounds of this invention retain the dimethyl groups of theophylline. The compounds of this invention are of the general formula,
Formula 1

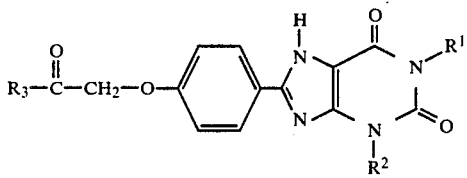

wherein
$R^1$ and $R^2$ = a carbon chain of 1-6 carbons;
$R^3$ = carboxylic acids (OH—), alkoxy, aryloxy, N-oxyimide; or
wherein
$R^3 = R^4R^5N$
wherein
$R^5$ is hydrogen, alkyl, aryl, or alkylaryl groups; and
wherein
$R^4 = R^5$ or $X(CH_2)^nNH$
wherein
X = primary, secondary, or tertiary amino group; or
secondary or tertiary amino group wherein one of the amine substituents is a p-hydroxybenzyl group; or
hydroxy or carboxy; or
acyl-amino group of the form $R^6CO$—;
wherein
$R^6$ is such that RCOOH = lower carboxylic acid, optionally substituted with at least one halogen; or
alpha-amino acid of the L or D configuration; or
N-benzyloxycarbonyl alpha-amino acid of the L or D configuration; or
biotin, optionally bonded through an amide linkage to a straight chain omega-amino acid having between 1 and 6 methylene groups; or
2-thiopheneacetic acid;
n = 1-10
and pharmaceutically acceptable salts.

The compounds of this invention are produced by processes described in the examples.

UTILITY STATEMENT

Selected compounds of this invention have shown significant activity as antiallergenic and antiasthmatic drugs by standard pharmacological tests. Theophylline and other xanthine derivatives are used clinically in the treatment of asthma, cardiac or renal failure, high blood pressure, and depression; i.e., conditions involving the inhibition or blocking of adenosine receptors. The present compounds are adenosine antagonists and, as such, are useful in the same manner as theophylline and other xanthine derivatives. Furthermore, the present compounds are more water-soluble and more potent than most known xanthine derivatives. Moderate selectivity depending on the nature of the group attached to the functionalized congener has been demonstrated, thus reducing the side effects associated with the administration of known adenosine receptor antagonists. Furthermore, the $A_1$-specific antagonists such as compound 6d are useful therapeutically in combination with a nonspecific adenosine agonist. The net effect of such a combination is decreasing blood pressure (an $A_2$ effect of the agonist) without a concomitant effect on the heart rate (since the $A_1$-agonist effect of slowing the heart rate would be cancelled by the specific antagonist). In short, some of the compounds of this invention, used in conjunction with adenosine analogs, are useful as hypotensives/vasodilators, antithrombotics, and selective central nervous system stimulants. Table 2 shows the solubility values of these compounds.

SPECIFIC DISCLOSURE

The compounds of the present invention are of the general formula:
Formula 1

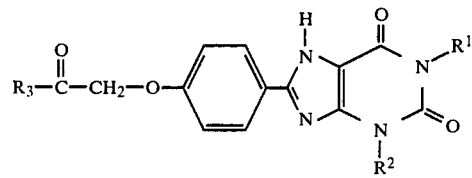

wherein
$R^1 R^2 = C_1 - C_6$ and
$R_3$ is any one of the 8-phenyl substituents illustrated in Table 1.

The general formula for the amino acid conjugates and oligopeptide conjugates (compounds 11-31) is:
Formula 2:

A—B where
A and B are linked together in an amide linkage, and where A (the primary pharmacophore) is:

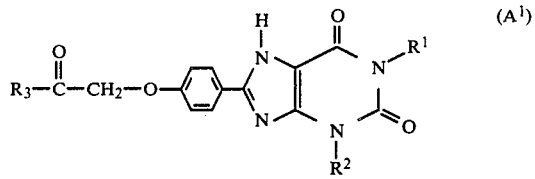

or

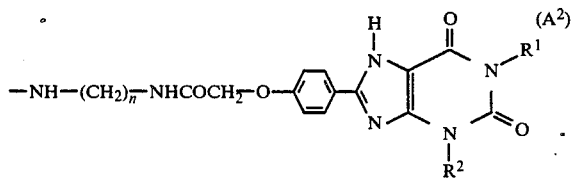

where
$R^1$ and $R^2$ are carbon chains of 1-6 carbons and
n = 2-6
and B (the carrier) is an amino acid of the L- or D-configuration or an oligopeptide consisting of 1-5 amino acids of the L- or D- configuration.

When $A = A^1$, the point of the A—B amide bond is at the terminal α-amino group of the carrier (B). The α-carboxylic acid group of the carrier (B) may be present as a free carboxylate or blocked by a conventional peptide protecting group (including, but not exclusively, the t-butyl ester group).

When $A = A^2$, the point of the A—B amide bond is at the terminal α-carboxyl group of carrier (B). The α- amino group of carrier (B) may be present as a free amine (or a pharmaceutically acceptable salt thereof), or blocked by a conventional peptide protecting group (including, but not exclusively, the t-butyloxycarbonyl or benzyloxycarbonyl groups).

The preferred compounds of this invention (Formula 1) are $R_1 = R_2 = (CH_2)_2CH_3$ and
$R_3 = H_2N-NHCOCH_2-O-$, (6g)
$\quad H_2N-(CH_2)_2NHCOCH_2-O-$, (6d)
$\quad H_2N-(CH_2)_8NHCOCH_2-O-$, (6e)

(8b)
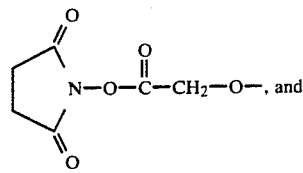

$HO_2C-CH_2$, (1b)

(5)
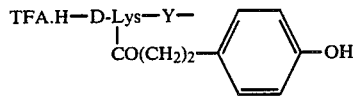

The preferred amino compounds corresponding to Formula 2 are:

HBr.H—(Gly)₂—Y— (15b)

TFA.H—L—Met—Y— (19b)

(HBr)₂.H—L—Lys(H)—Y— (20b)

HBr.H—D—Lys(H)—Y— (21d)

TFA.H—D—Lys—Y— (23b)

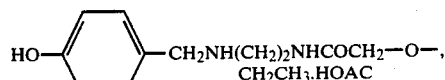 (23b)

TFA.H—L—Cit—Y— (24b)

HBr.H—L—Tyr—Y— (26b)

(HBr)₂.H—D—Tyr—D—Lys(H)—Y— (29b)

TFA.H—L—Tha—Y— (31b)

where
Y =

$$-NH(CH_2)_2-NH-\overset{O}{\underset{\|}{C}}-CH_2-O$$

Gly = glycyl
TFA = CF₃COOH
Lys = lysyl
Cit = citrulline, H₂NCONH(CH₂)₃CH—(NH₂-)COOH
Tyr = tyrosyl
Tha = 3(2'-thienyl)alanyl,

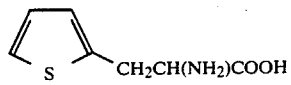

All of these compounds combine high potency with high solubility. The solubility value is partly due to the covalent attachment of polar groups (i.e., para substituents on the 8-phenyl ring) noted above and is therefore not intended to be limited by the polar groups specifically designated. Examples of the compounds of this invention, as well as their activity and solubility are set out in Table 1.

Biological activity at the A₂-receptor is measured by inhibition of 2-chloroadenosine-stimulated cyclic-AMP formation in guinea pig brain slices. The results for selected analogs are summarized in Table 1A. Many of the free amino conjugates show a high degree of selectivity for A₁-receptors. Among the most selective are conjugates of methionine, phenylalanine, thienylalanine, tyrosine.

Many of the highly potent A₁-antagonists also exhibit greatly enhanced water solubility. Upon attachment of citrulline to the amino congener the aqueous solubility (pH 7.2, 0.1 M sodium phosphate) rose from 90 micromolar to 250 micromolar. The neutral, polar side chain of citrulline improves water solubility in oligopeptides. The lysine conjugates, with an additional ammonium group on the carrier, displayed an aqueous solubility of 350 micromolar. This is in contrast to 3.2 micromolar solubility measured for 1,3-dipropyl-8-p-hydroxyphenylxanthine. The favorable water solubility made possible effective HPLC for analytical and semi-preparative purposes using a C-18 bonded silica column with 50–65% methanol in aqueous buffers (easing laboratory purification of these compounds). Octanol/water partition coefficients which demonstrate further the improved polarity characteristics of the amino acid conjugates are given in Table 4.

Polar groups that promote water solubility and are uncharged at physiological pH include carboxamide, ureido, alcohol, amide, ether, carbamate, nitrogen heterocycle, hydrazide, and sulfonamide. Charged polar groups include alkylamino, carboxyl, sulfonate, guanidine, phosphate, metal salts and their complexes. See particularly Table 1 for xanthine analogs containing amino acids (compounds 12–31).

IC₅₀ values for A₁-receptors were obtained from antagonism of binding of 1 nM [³H]cyclohexyladenosine to rat cerebral cortical membranes. IC₅₀ values for A₂-receptors were obtained from antagonism of [³H]cyclic-AMP accumulation elicited by 15 uM 2-chloroadenosine in [³H]adenine-labeled guinea pig cerebral cortical slices. K$_i$ values were calculated from the equation K$_i$=IC₅₀/(1+conc. of adenosine analog/Ka for adenosine analog).

The ratio of A₂ to A₁ indicates the degree of specificity of the particular compound (low values represent high A₂-receptor specificity). The compounds with A₂-specificity are expected to be more useful as anti-allergenic or anti-asthmatic agents. Compounds with high A₁ specificity in general block the cardiac depressant effects of adenosine without diminishing blood flow to the heart, thus they may be more useful therapeutically in treating cardiac insufficiency and angina. Some analogs are expected to have activity as inhibitors of phosphodiesterase, as do theophylline and caffeine, thus contributing anti-allergenic and anti-asthmatic activity. The solubility of these compounds is also shown and should be noted as an index to a compound's medicinal value—a compound that does not dissolve in water cannot be used therapeutically. If the ratio of $A_2$ to $A_1$ is low, the compound is $A_2$-selective and is anti-allergenic or anti-asthmatic (without cardiovascular effects). The ideal ratio is about 0.1 or less, but this has never been achieved. The most selective $A_2$ antagonists known prior to this invention is about 0.6. Note that preferred compounds 1b and 6g are more selective.

If the ratio of $A_2$ to $A_1$ is high, the compound is $A_1$-selective and exhibits lipolytic, central stimulant, and cardiac stimulant properties. Most known compounds of interest are no lower than 10. Note that many of the compounds of this invention are significantly higher than 10.

Compounds bearing multiple charged groups (such as 20b and 21d) or permanently charged groups do not penetrate cells and thus are not active as inhibitors of phosphodiesterase. Moreover, they do not pass the blood-brain barrier. This adds an additional degree of selectivity to the action of $A_1$-selective compounds, which means fewer side effects in vivo. The effect of non-penetration is similar to that observed previously for p-sulfophenylxanthines, which are not $A_1$-selective.

One class of congeners, the analogs bearing a distal amino group and capable of introducing a wide range of substituents on an amino-functionalized chain, exhibit water solubility and partition characteristics which allow these compounds to be absorbed into a human or animal circulatory system after intraperitoneal injection. These analogs comprise an amino acid carrier linked through an amide bond to a functionalized xanthine congener. This distal amino group may be as many as 14 bond lengths from the phenyl ring. As shown in Tables 3 and 4, these analogs may be either free amino conjugates or amino-protected intermediates. In general, the attached carrier (amino acid group or oligopeptide) substantially affects the overall solubility of the analog, increasing solubility by approximately 10,000 fold.

The attachment of free amino acids to the chain not only favors high potency in these adenosine conjugates but has led to improved solubility characteristics due to the presence of the amino group, which is predominantly charged at physiological pH. It has been observed that frequently the 8-phenylxanthine analogs noted for high potency, such as 8-phenyltheophylline, are too hydrophobic to be absorbed into circulation after intraperitoneal injection. This is not a limitation in the compounds of this invention, which combine nanomolar potency with greatly increased water solubility ($K_i$ at $A_1$-receptors and maximum aqueous concentration differ by a factor of approximately $10^4$). As expected, the attached carrier in general may have a substantial effect on the overall solubility of the analog even in organic solvents. For example, compound 13a, containing two bulky hydrophobic groups on a lysine residue, is freely soluble in ethyl acetate, in contrast to smaller analogs.

The wide range of incorporated amino acid side chains that lead to high potency suggests considerable versatility in this approach for constructing receptor probes and labels. The conjugates of tyrosine (26b and 28b), tryptophan (30b), and the unnatural amino acid thienylalanine (31b) may be iodinated by virtue of electron rich aromatic rings (see also Example 14).

The fact that high potency was observed for a simple dipeptide conjugate (15b) and the corrsponding protected intermediate (15a) indicates that monodisperse oligopeptides are suitable covalent carriers for the xanthines as adenosine receptor antagonists. Previously, oligopeptide conjugates of isoproterenol were noted to have increased potency and prolonged duration of action in vivo. Linkage of a functionalized drug congener to amino acids or peptides as carriers has advantages in the design of new analogs. The variety of side chains available allows great flexibility in the charge, steric characteristics, hydrophobicity, and functionality of the carrier. These side chains are well known to the practitioner and may be incorporated in the compounds of this invention as specific carriers which favorably alter the physical and/or pharmacological properties of a drug.

Synthetic Methods

The carboxylic acid congener of theophylline (1a), its dipropyl analog (1b), and the other 1,3-dialkyl analogs are synthesized by a standard approach to xanthines, as described in U.S. Pat. No. 4,452,788. Briefly, 5,6-diamino-1,3-dimethyluracil (leading to compounds in which $R^1=R^2=CH_3$) is commercially available, but other 1,3-dialkyl compounds are prepared with appropriate dialkyl urea and cyanoacetic acid. These reactions are decribed in *J Org. Chem.*, Vol. 16, p. 1879 (1951) and *Can. J. Chem.*, Vol. 46, p. 3413 (1968). The imidazole ring is formed by oxidative closure of the benzylidene adduct derived from the appropriate diaminouracil and a substituted benzaldehyde (Example 1). 4-(Carboxymethyloxy) benzaldehyde (Compound A) is the product of alkylation of p-hydroxybenzaldehyde by iodoacetate.

Ring closure of the benzylidene adduct occurs by heating with substoichiometric amounts of anhydrous ferric chloride. In the case of the carboxylic acid derivatives, considerable ethyl ester (3) is formed using ethanol as a solvent. To avoid separating the mixture of acid and ethyl ester, the esterification is brought to completion by prolonged heating of the reaction mixture in the presence of one equivalent of ferric chloride. Use of trifluoroethanol as the solvent during ring closure produces 1 exclusively. Compound 1 may alternatively be prepared by basic hydrolysis of the ester (3).

Coupling of the carboxylic acid congeners to amines using carbodiimides presents problems due to limited solubility. Attempts to couple 8b to various polar amines using carbodiimides in dimethylformamide often results in isolation of the N-acylurea (4) derived from the acid and the coupling reagent. Compound 1a is coupled in low yield to p-toluidine. In an alternate approach to amide formation, the N-hydroxysuccinimide ester (5) of the carboxylic acid congener is prepared and is readily separable from the N-acylisourea by crystallization. The N-hydroxysuccinimide esters and the water-soluble esters of N-hydroxy-2-sulfosuccinimide of the carboxylic acid congeners are activated forms of the drug for coupling to amines, including biopolymers such as proteins, to serve as drug carriers. These drug derivatives may also be attached to directed carriers such as monoclonal antibodies.

Alternatively, an amide bond may be introduced on the substituted benzaldehyde (as in Example 1) prior to formation of the imidazole ring.

The ethyl ester (3) may be aminolyzed by excess unhindered amines in dimethylformamide to form amides (6). Aminolysis by alkyl diamines produces the functionalized amino congeners (6d, 6e), which are the basis for additional derivatives including amides (7 and 8) and secondary and tertiary amines (9), made via reductive amination. See the examples for additional description of these synthesis procedures.

The amino congeners of 1,3-dialkylxanthine derived from ethylene diamine, e.g., 6d, are coupled to various urethane protected amino acids by the active ester method. Protected amino acid conjugates 13 through 31 were synthesized by the coupling methods specified in Table 3, following the general procedures noted above. Active ester derivatives of glutamine, leucine, and phenylalanine were obtained from Sigma. Protected amino acid derivatives of citrulline and methionine were from Bachem, and derivatives of asparagine, glycine, and glycylglycine were from U.S. Biochemical Corporation.

Some protected amino acid derivatives were prepared. Representative examples are as follows:

t-Butyloxycarbonyl-D-tyrosine N-hydroxysuccinimide ester (32) is prepared from the Boc-D-tyrosine (Chemical Dynamics), N-hydroxysuccinimide, and dicyclohexylcarbodiimide (DCC) in dimethylformamide (DMF) in 95% yield.

t-Butyloxycarbonyl-L-3-(2'-thienyl)alanine (33) is prepared from L-3-(2'-thienyl)alanine (Chemical Dynamics) and di-t-butyl-dicarbonate by standard methods. The product is isolated as a clear oil (yield 95%).

t-Butyloxycarbonyl-L-3-(2'-thienyl)alanine N-hydroxysuccinimide ester (34) is prepared from compound by the DCC method in 84% yield. These compounds are intermediates of the formula set out below:

TABLE A

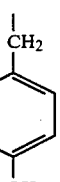

| $R^1$ | $R^2$ | $R^3$ | |
|---|---|---|---|
| 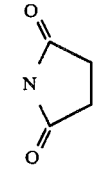 | H | O<br>N<br>O | 32 |
| H | 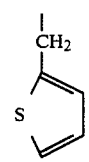 | H | 33 |
| H | 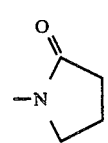 | O<br>—N<br>O | 34 |

Some protected amino acids and active ester intermediates used in the synthesis of conjugates.

Deblocking of acid-labile protecting groups is carried out for one hour at room temperature in anhydrous 48% HBr in acetic acid for carbobenzoxy- (Cbz-) derivatives and in neat trifluoroacetic acid for t-butyloxycarbonyl- (Boc-) derivatives. Compounds 19a and 30a were deprotected in the presence of thiophenol. After evaporation, the residue is triturated with ether, and the solid product is collected, washed with ether, and dried under vacuum. The purity of the xanthine analogs is checked by thin layer chromatography in chloroform/methanol/acetic acid (85/10/5 or 50/50/5), and, if necessary, the product is recrystallized from dimethylformamide/ether or methanol/ether. Since N-hydroxysuccinimide esters and p-nitrophenyl esters of the protected amino acid are used, minimal side chain protection is required (e.g., in the cases of tyrosine and asparagine). During the reaction in dimethylformamide, the amino congener dissolves gradually as the acylation proceeds, thus excess base which might lead to racemization of the amino acid is minimized. The urethane protecting groups are subsequently cleaved in acid without serious side reactions on the xanthine portion of the molecule.

Biological Activity

The 1,3-dialkyl-8-(p-hydroxyphenyl)xanthine, from which the functionalized congeners are formalistically derived, have been shown in earlier studies to be potent antagonists of $A_1$- and $A_2$-adenosine receptors [PNAS, Vol. 77, p. 5547 (1980)]. 8-p-Hydroxyphenyltheophylline is 280-fold more potent than theophylline in displacing [$^3$H]cyclohexyladenosine from $A_1$-adenosine receptors in rat cerebral cortical membranes and is 107-fold more potent than theophylline in antagonizing $A_2$-adenosine receptor mediated activation of cyclic AMP-generation by 2-chloroadenosine in guinea pig cerebral cortical slices. Replacement of the 1,3-dimethyl groups with n-propyl groups yields 1,3-dipropyl-8-(p-hydroxyphenyl)xanthine (2b). This analog is an extremely potent $A_1$-adenosine antagonist with a $K_i$ value versus [$^3$H]cyclohexyl-adenosine binding in rat cerebral cortical slices of 2.9 nM. The change in the alkyl residues, thus, has increased potency at $A_1$-receptors by about 17 fold. The change in alkyl residues also increases potency at $A_2$-receptors but to a much lesser extent (2.6-fold), yielding a somewhat selective $A_1$-antagonist.

Functionalization of these two xanthines is based on the presence of a p-carboxymethyloxy residue on the 8-phenyl ring. This functionalization permitted facile synthesis of a wide variety of amides. In the case of the 8-phenyltheophyllines, the p-carboxymethyloxy compound (1a) has a ten-fold lower activity than the p-hydroxy compound at $A_1$-receptors and a 3.3-fold lower activity at $A_2$-receptors (Table 1). It appears likely that the presence of the anionic carboxyl group is not favorable to high affinity binding to either receptor. With an anionic p-carboxyl group directly on the 8-phenyl ring, even lower activity pertained with $K_i$ values of 3000 nM at $A_1$-receptors and 2500 nM at $A_2$-receptors. A p-toluide function (2a) was well tolerated by both $A_1$ and $A_2$-receptors, and this neutral derivative of a functionalized congener was about 2-fold more potent than 8-(p-hydroxyphenyl)theophylline at $A_1$-receptors and about 6-fold more potent at $A_2$-receptors (Table 1).

Further syntheses of functionalized congeners were based on the higher potency and selectivity of 1,3-dipropyl-8-(p-hydroxyphenyl)xanthine relative to the 1,3-dimethyl homolog which enhances the activity of the p-carboxymethyloxy congeners and derivatives even further. In this series the p-carboxymethyloxy compound is 20-fold less potent than the p-hydroxy compound at $A_1$-receptors. At $A_2$-receptors the p-carboxymethyloxy compound is nearly equipotent with the p-hydroxy compound. Again, it appears likely that the presence of the anionic carboxy group mitigates against high activity at the $A_1$-receptors. Similarly, 8-p-carboxy-1,3-dipropylxanthine is about 60-fold less active than the p-hydroxy compound at $A_1$-receptors, while being only 2-fold less active at $A_2$-receptors nearly identical to that of the anionic carboxylic acid. The carboxamide (6a) is very active at $A_1$-receptors and moderately selective, being 8-fold more active at $A_1$-receptors than at $A_2$-receptors. Remarkably, the p-toluide (2b) is no more potent than the acid at $A_1$ receptors, while being 22-fold less potent than the acid at $A_2$-receptors. This finding stands in direct contrast to results obtained with the analogous compounds in the theophylline (1,3-dimethyl) series, in which series the p-toluide was about 20-fold more active than the acid both at $A_1$-receptors and at $A_2$-receptors. It is believed that contributions to affinity afforded by the 1,3-dialkyl substituents and by para-substituents on the 8-phenyl ring are not independent and can greatly influence each other in either a positive or a negative manner. For example, the p-hydroxyanilide (2c) is nearly 10-fold more potent than the p-toluide at both $A_1$- and $A_2$-receptors, thus illustrating the potential importance of minor structural modifications distant from the primary pharmacophore (in this case the 8-phenylxanthine) on biological activity. The o-hydroxy-m-sulfoanilide (6f) is synthesized as a water-soluble xanthine suitable for radioiodination. It is not selective, and its potency was at least three-fold less than the parent acid.

The aminoethylamide (6d) is synthesized with a view of increasing water solubility and also of providing a key intermediate for preparation of affinity columns, fluorescent probes and a biotin-containing xanthine. The aminoethylamide is very potent at $A_1$-adenosine receptors with a $K_i$ value 1.2 nM. It was some forty-fold less potent at $A_2$-adenosine receptors. The presence of a p-hydroxybenzyl and ethyl substituents (9b) (phenol suitable for radioiodination) on the terminal amino group exhibits little effect on the potency at $A_1$-receptors, while reducing potency at $A_2$-receptors by over four-fold. This compound is among the most selective $A_1$-antagonist (145-fold) in the present series.

A number of compounds were prepared in which the terminal amino group was acylated. The acetyl compound (7a) is 20-fold less potent than the parent amine at $A_1$-receptors while the biotinyl compound (7d) is 45-fold less potent. Potency at the $A_2$-receptor is not significantly affected in the case of the acetyl compound, while potency for the biotinyl compound is reduced at $A_2$-receptors by only three-fold. Both acyl compounds are, thus, relatively nonselective antagonists for $A_1$- and $A_2$-adenosine receptors in contrast to the parent amine that exhibits a 40-fold selectivity for $A_1$=receptors. The potency of the acetyl compound suggests that affinity columns prepared through acyl coupling to the amino compound could be effective in isolation of solubilized $A_1$- and $A_2$-receptors and/or xanthine-binding sites.

The use of longer spacer chains appears feasible for preparation of affinity columns if the aminoethylamide proves unsatisfactory. The aminooctylamide (6e) was only 5-fold less potent than the aminoethylamide (6d) at $A_1$-receptors and about 2-fold less potent at $A_2$-receptors.

A bulky ureide (4) was found to have relatively low activity at both $A_1$- and $A_2$-receptors.

The compounds of the invention form pharmaceutically acceptable salts with both organic and inorganic acids and bases. Examples of suitable acids for salt formation are hydrochloric, sulfuric, phosphoric, acetic, citric, oxalic, malonic, salicylic, malic, fumaric, succinic, ascorbic, maleic, methansulfonic, and the like. The salts are prepared by contacting the free base form with an equivalent amount of the desired acid in the conventional manner. Examples of suitable bases for salt formation are sodium hydroxide, sodium carbonate, sodium bicarbonate, potassium hydroxide, calcium hydroxide, ammonia, organic amines, and the like. The salts are prepared by contacting the free acid form with an equivalent amount of the desired base in the conventional manner.

In summary, the functionalized congener approach to xanthine antagonists for adenosine receptors has yielded a series of potent compounds which in some cases are moderately selective for $A_1$- or $A_2$-receptors. The effects on biological activities caused by modifications of functions distal from the primary pharmacophore in some cases are quite impressive. Dramatically high potency at the $A_1$-receptor is associated with the presence of an alkyl amino group on the chain attached to the 8-phenyl ring.

Affinities of congeners and derivatives for the $A_1$-receptors seems somewhat more sensitive to distal modifications than affinities for the $A_2$-receptor. As yet no completely selective $A_2$-receptor antagonists have been discovered and as yet no completely specific $A_1$-receptor antagonists are available. The present set of functionalized xanthines are improved analogs of theophylline and caffeine and will thus have more selective antiasthmatic, diuretic, respiratory stimulant, central stimulant, cardiac stimulant, analgesic adjuvant, and anti-inflammatory applications.

EXAMPLES

In all of the following examples, thin layer chromatography (TLC) was carreid out using Analtech silica gel GF plates using mixtures of chloroform/methanol/acetic acid (v/v; A: 50/50/5; B: 94/4/2). Reagent grade dimethylformamide (DMF, Aldrich gold label) was stored over 3 Å molecular sieves. Proton NMR spectra were taken on a Varian 220 MHz instrument in the Fourier transform mode. Dicyclohexylcarbodiimide (DCC) was purchased from Sigma. 5,6-Diaminouracil hydrate in Example 3 was purchased from Aldrich.

EXAMPLE 1

4-(Carboxymethyloxy)benzaldehyde (A)

To a solution of p-hydroxybenzaldehyde (49 g, 0.40 mol) were added iodoacetic acid (75 g, 0.40 mol) and potassium carbonate (anhydrous, 120 g), and the magnetically stirred mixture was warmed at 60° C. for three days. The resulting solid was dispersed mechanically in a mixture of ethyl acetate (400 ml) and water. The mixture was neutralized cautiously with phosphoric acid. After the dissolution of the solid mass, the neutral aqueous layer was withdrawn. The organic layer was extracted repeatedly with a concentrated solution of dibasic sodium phosphate, to remove additional acidic organic material. The aqueous extracts were combined, filtered through glass wool, and acidified to pH 1 using 6N HCl. This solution was placed in the refrigerator overnight, and a product of tan crystals (21.85 g) was collected. Unreacted p-hydroxybenzaldehyde was recovered upon evaporation of the organic layer. Yield based on recovery of starting material was 60%. Mp 191°–193° C. Analysis ($C_9H_8O_4$): calc. 60.00% C, 4.48% H; found 59.66% C, 4.37% H.

4-(Carboxymethyloxy)benzaldehyde p-toluide

Dicyclohexylcarbodiimide (DCC, 1.32 g, 6.4 mmol) was added to a solution of compound A (1.15 g, 6.4 mmol) in tetrahydrofuran (50 ml). After stirring for ten minutes p-toluidine (0.7 g, 6.5 mmol) was added. After one hour, the precipitate was removed by filtration, and the filtrate was reduced in volume by evaporation. A crystalline product (1.09 g, 63% yield) was obtained by trituration of the filtrate with petroleum ether. An analytical sample was obtained by thin layer purification (solvent B) which was necessary for the removal of a faster moving impurity, later shown by C,H,N analysis to be the imine adduct of the product with p-toluidine.

4-(Carboxymethyloxy)benzaldehyde p-hydroxyanilide

Compound A (1.80 g, 10 mmol) was dissolved in 25 ml of tetrahydrofuran containing 20% DMF. To this solution were added DCC (2.06 g, 10 mmol) and after ten minutes a solution of p-aminophenol hydrochloride (1.46 g, 10 mmol) and triethylamine (0.78 g, 10 mmol) in DMF (10 ml). After 2 hours the precipitate was removed by filtration and washed with tetrahydrofuran. The combined filtrates were evaporated and triturated with water. A yellow oil separated and crystallized, providing 2.40 g (89%) of product. The product was recrystallized from ethanol/petroleum ether to give a white solid which melted at 185°–186° C. Analysis ($C_{15}H_{13}NP_4$): calc. 66.41% C, 4.83% H, 5.16% N; found 66.11% C, 5.07% H, 5.36% N.

EXAMPLE 2

6-Amino-1,3-dipropyl-5-(4'-carboxymethyloxybenzylideneamino)uracil

A representative synthesis of benzylidene adduct is given. Compound A (1.51 g, 8.37 mmol) was dissolved in a mixture of methanol (35 ml) and acetic acid (5 ml) in a 50 ml boiling flask on a steam bath. To this was added a methanolic solution (60 ml) of freshly synthesized 5,6-diamino-1,3-dipropyluracil. After heating 15 minutes, the volume was reduced by evaporation until crystallization occurred. Ether (40 ml) was added and the nearly white solid was collected. Yield 2.80 g (86%), mp 179°–180° C. Analysis ($C_{19}H_{24}N_4O_5$): calc. 58.60% C, 6.21% H, 14.39% N; found 58.72% C, 6.16% H, 14.43% N.

EXAMPLE 3

8-(4'-Carboxymethyloxphenyl)-1,3-dimethylxanthine (1a)

The benzylidene adduct was prepared as described in Example 2 from compound A (0.609 g, 3.38 mmol) and 5,6-diamino-1,3-dimethyluracil hydrate (0.58 g, 3.4 mmol). Tan crystals (0.963 g, 85.7%) were obtained upon cooling the reaction mixture overnight in the refrigerator. The benzylidene adduct (98 mg), used without further purification, was dissolved in warm DMF (7 ml), treated with ferric oxide (20 mg) and heated on the steam bath for four hours. After adding an equal volume of ethanol, the precipitate was collected and dried. Yield 76 mg (67% overall yield), not melting up to 310° C.

EXAMPLE 4

8-(4'-Carboxymethyloxyphenyl)-1,3-dipropylxanthine (1b)

Method A: The benzylidene adduct (191 mg, 0.49 mmol) was suspended in trifluoroethanol (15 ml) and dissolved by refluxing on a steam bath. Anhydrous ferric chloride (20 mg) was added and heating was continued for two hours. Ether was added to complete the precipitation of product, which was collected and dried in vacuo. The crude product, 0.17 g (89%), was recrystallized from DMF/methanol/ether to give analytically pure material, mp 283°–285° C. Analysis ($C_{19}H_{22}N_4O_5$): calc. 59.06% C, 5.74% H, 14.50% N; found 59.03% C, 5.33% H, 14.24% N.

Method B: The ethyl ester (114 mg, 0.28 mmol) was dissolved in DMF (5 ml) and treated with sodium carbonate (5 ml, 0.1N). The mixture was heated on the steam bath for one-half hour. The solvent was evaporated, leaving a white film, which was triturated with dilute HCl. The resulting white precipitate was collected and washed with water and dried in vacuo. This material was homogeneous by TLC (solvent B; $R_f$ 0.42) and identical to the product prepared by method A. Yield 105 mg (99%).

EXAMPLE 5

8-(4'-Carboxymethyloxyphenyl)-1,3-dipropyl xanthine 4-methylanilide (2b)

The p-toluide of the carboxylic acid congener (1b) was prepared by the method described below for compound 2c, except that the reaction was continued overnight.

8-(4'-Carboxymethyloxyphenyl)-1,3-dipropyl xanthine 4-hydroxyanilide (2c)

The benzylidene adduct formed from freshly prepared 5,6-diamino-1,3-dipropyluracil (see Example 2) (0.385 mmol) and the substituted benzaldehyde (88 mg, 0.325 mmol) was formed according to the method described for the compound in Example 2. The solid adduct (0.14 g, 90% yield) was dissolved in hot absolute ethanol (10 ml), treated with ferric chloride (20 mg) and heated on the steam bath until the product precipitated (30 min). Ether was added and the product (93 mg, 60% overall yield from 5,6-diamino-1,3-dipropyluracil and 4-(carboxymethyloxy)benzaldehyde) was isolated.

EXAMPLE 6

8-(4'-Carboxymethyloxyphenyl)-1,3-dipropylxanthine ethyl ester (3)

The compound from Example 2 (1.69 g, 4.3 mmol) was suspended in 100 ml absolute ethanol. Anhydrous ferric chloride (0.70 g, 4.3 mmol) was added, and the mixture was refluxed on a steam bath for one day. The slow conversion of the free acid (identical to compound 1b, $R_f$ 0.35) to the ethyl ester ($R_f$ 0.78) was followed by TLC on silica gel using solvent B. The reaction mixture was evaporated in vacuo to a small volume, and dry ether was added. The bulky crystalline mass was collected by filtration, washed with ether, and dried in vacuo. Yield 1.27 g (70.8%), mp 243°–244° C. Analysis ($C_{21}H_{26}N_4O_5$): calc. 60.86% C, 6.23% H, 13.51% N; found 60.42% C, 5.80% H, 13.50% N.

EXAMPLE 7

8-(4'-Carboxymethyloxyphenyl)-1,3-dipropylxanthine N-hydroxysuccinimide ester (5)

The carboxylic acid congener (compound 1b, 18.4 mg, 0.048 mmol) was dissolved in DMF (5 ml), cooled in an ice bath, and treated with N-hydroxysuccinimide (6 mg) and DCC (11 mg). After stirring for one day at room temperature, the urea was removed by filtration. Upon addition of water, a white solid precipitated and was collected. Recrystallization from DMF/water provided 11.1 mg of the pure product (48% yield). A side product removed by crystallization was identical to the N-acyl urea.

EXAMPLE 8

8-(4'-Carboxymethyloxyphenyl)-1,3-dipropyl xanthine 2-aminoethylamide (6d)

Compound 3 (57.5 mg, 0.14 mmol) was dissolved in warm dimethylformamide (1.0 ml). Upon reaching room temperature ethylene diamine (1.0 ml) ws added. After stirring overnight most of the solvent was evaporated under a stream of nitrogen. The resulting oil was triturated with methanol. After crystallization began, ether was added and the product was collected and dried. Yield 59 mg (99%), melting at 214°–216° C. with decomposition, homogeneous by TLC (solvent system A).

EXAMPLE 9

8-(4'-Carboxymethyloxyphenyl)-1,3-dipropylxanthine 2-(biotinylamino)ethylamide (7d)

Compound 6d (24.1 mg, 0.056 mmol) was suspended in 1 ml DMF. N-Hydroxysuccinimido-d-biotin (Sigma, 23.6 mg, 0.069 mmol) was added with stirring. A solution formed after several minutes, and a precipitate appeared soon thereafter. After one day methanol (1 ml) and ether were added. The precipitate was collected and dried (yield 26.6 mg, 73%).

EXAMPLE 10

(A)

8-(4'-Carboxymethyloxyphenyl)-1,3-dipropylxanthine 2-(N-4'-hydroxybenzyl-N-ethylamino)ethylamide acetate (8b)

Compound 6c (56 mg, 0.13 mmol) and 4-hydroxybenzaldehyde (19 mg, 0.16 mmol) were dissolved in warm acetic acid (5%) in ethanol (2 ml) and heated on a steam bath for two hours. The solvent was evaporated and the residue triturated with ether to give 9b, a tan solid (75% yield). NMR (ppm, DMSO, $d_6$): 8.15 (s,1H,CH=N), 8.05 and 7.04 (each d,2H,8-phenyl,J-8.9 Hz), 7.55 and 6.78 (each d,2H,phenol, J=8.5 Hz), 4.56 (s,2H,$CH_2O$), 3.59 ($CH_2N$), 1.91 (s,3H,acetate), and signals from propyl groups. Analysis ($C_{30}H_{36}N_6O_7$) calc: 60.80% C, 6.12% H, 14.18% N; found: 60.93% C, 5.95% H, 14.12% N.

(B)

8-(4'-Carboxymethyloxyphenyl)-1,3-dipropylxanthine 2-(N-4 -hydroxybenzyl-N-ethylamino)ethylamide acetate (8b)

Compound 8b (8.7 mg, 0.015 mmol) was suspended in methanol (1 ml) and treated with excess sodium cyanoborohydride (20 mg, 0.32 mmol). The mixture was warmed at 60° C. to form a solution and treated with acetaldehyde (0.03 ml). After two hours the solvent was evaporated and the residue was chromatographed on LH-20 eluting with methanol. Evaporation of the solvent left a clear film of 16 (5.9 mg, 61%). The product was chromatographically pure ($R_f$ 0.45, Analtech RPS-F, 75% MeOH/5% HOAc/$H_2O$, positive Pauly reaction, unreactive towards ninhydrin). An average molecular weight of 563 was determined by californium plasma desorption mass spectroscopy.

EXAMPLE 11

Biochemical assays.

Inhibition of binding of 1 nM [$^3$H]$N^6$-cyclohexyladenosine to $A_1$-adenosine receptors in rat cerebral cortical membranes was assayed as described in Daly et al, Cell. Mol. Neurobiol., Vol. 3, p. 6 (1983). Inhibition of binding by a range of concentrations of each xanthine was assessed in triplicate for at least two separate experiments. Inhibition of 2-chloroadenosine-stimulated cyclic AMP accumulation in [$^3$H]adenine-labeled guinea pig cerebral cortical slices was assayed essentially as described in the Daly et al article, supra. In the present experiments 10 ug/ml of adenosine deaminase was present in incubations with slices to prevent effects of endogenous adenosine, and 30 uM 4-(3-cyclopentyloxy-4-methoxyphenyl)-2-pyrrolidone (rolipram, ZK 62711) was present to inhibit phosphodiesterases. Under these conditions 2-chloroadenosine elicited a maximal 10–20 fold increase in levels of radioactive cyclic AMP in guinea pig cortical slices with an $EC_{50}$ of about 8 uM. Inhibition of the response to 15 uM 2-chloroadenosine by a range of concentrations of each xanthine was assessed in triplicate in at least two separate experiments.

EXAMPLE 12

The following are also representative of the claimed invention and may be synthesized in generally the same manner as shown in the preceeding examples.

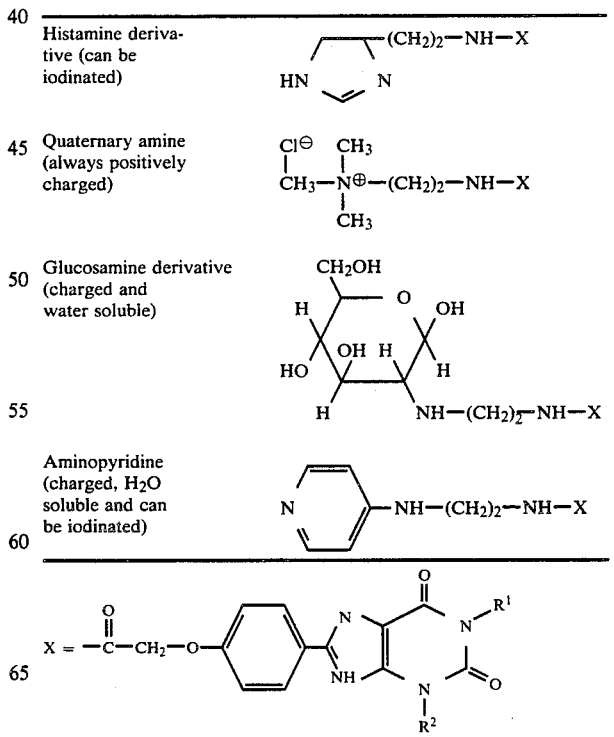

EXAMPLE 13

The free amino conjugates and the amino-protected intermediates were screened for the ability to compete against [$^3$H]-cyclohexyladenosine (CHA) in rat cerebral cortex homogenates. The binding affinity constants are shown in Table 4. A pattern appeared in which analogs with a free amino group on the chain exhibited high potency. In this series the amino group was located at between 8 and 14 bond lengths from the phenyl ring, and the receptor binding affinity was in the $10^{-9}$ to $10^{-8}$ molar range. In most cases the activity of the blocked intermediate was less than that of the free amino analog. The carbobenzoxy- (Cbz-) protected conjugates tended to be of moderate potency, and t-butyloxycarbonyl- (Boc-) protected conjugates (of different amino acids) fell into a less potent range ($K_a$ greater than 20 nM). The protected dipeptide conjugate (of Cbz-glycylglycine) was of exceptionally high potency ($K_a=0.95$ nM) relative to other amino-protected conjugates.

EXAMPLE 14

A radioiodinated analog of theophylline was needed for studies on the adenosine receptor in tissues where it occurs in low levels. By attachment of the functionalized congener to a molecule which is subject to facile iodination, such as a phenol, this may be achieved. A substituted phenol was attached to an amino congener of 1,3-dipropyl xanthine resulting in binding affinity for the $A_1$ adenosine receptor in the nanomolar range.

The preliminary success towards the radioiodination of xanthines provides a general approach to the design of radiolabelled drug analogs (specifically, radiolabeled ligands for receptors for transmitters and hormones) based on the functionalized congener approach. A functionalized drug congener may be attached to a molecule specifically designed to accept a particular radioisotope. By treating separately the receptor recognition moiety contained in the congener and the chemistry of the radioisotope acceptor unit, one has more freedom to design schemes for efficient reactions with radioisotopes. A preferred compound for radiolabeling is compound 26b.

EXAMPLE 15

The melting point of some of the compounds of this invention were determined as follows:

| Compound | Melting Point (°C.) |
| --- | --- |
| 1a | >310 |
| 1b | 283–285 |
| 2a | 287–290 |
| 2b | >300 |
| 2c | >320 |
| 3 | 243–244 |
| 4 | >190 |
| 5 | 241–245 |
| 6a | 301–303 |
| 6c | 227–231 |
| 6d | 218–220 |
| 6e | >300 |
| 6g | >310 |
| 7a | 309–312 |
| 7d | 262–264 |
| 7e | 218–221 |
| 10 | 180–185 |
| 15b | decomp. 260–295 |
| 15c | 210–212.5 |
| 18b | 222–226 |
| 19b | 217–219 |
| 20b | 217–220 |
| 21d | decomp. 211–214 |
| 23b | 186–192 |
| 24b | 132–136 |
| 25b | 187–192 |
| 26b | decomp. 180–184 |
| 29b | decomp. 207–220 |
| 31b | 185–189 |

TABLE 1

| Compound | 8-Phenyl Substituent | $K_i$ (nM) $A_1$-Receptor | $K_i$ (nM) $A_2$-Receptor | $A_2/A_1$ Ratio | Name |
|---|---|---|---|---|---|
| 1a* | HOC(=O)—CH₂—O— | 500 ± 200 | 430 ± 80 | 0.86 | 8-(4'-carboxymethyloxyphenyl)-1,3-dimethyl-xanthine |
| 1b | HO—C(=O)—CH₂—O— | 58 ± 3 | 34 ± 13 | 0.59 | 8-(4'-carboxymethyloxyphenyl)-1,3-dipropyl-xanthine |
| 2a* | 4-CH₃-C₆H₄-NHCOCH₂—O— | 26 ± 5 | 20 ± 7 | 0.77 | 8-(4'-carboxymethyloxyphenyl)-1,3-dimethyl-xanthine |
| 2b | 4-CH₃-C₆H₄-NHCOCH₂—O— | 36 ± 23 | 750 ± 370 | 21.0 | 8-(4'-carboxymethyloxyphenyl)-1,3-dipropyl-xanthine-4-methylanilide |
| 2c | 4-HO-C₆H₄-NHCOCH₂—O— | 4.1 ± 1.5 | 62 ± 37 | 15.0 | 8-(4'-carboxymethyloxyphenyl)-1,3-dipropyl-xanthine-4-hydroxyanilide |
| 3 | CH₃CH₂OCO—CH₂—O— | 42 ± 3 | 30 ± 12 | 0.71 | 8-(4'-carboxymethyloxyphenyl)-1,3-dipropyl-xanthine ethyl ester |
| 4 | (C₆H₁₁)NHCON(C₆H₁₁)—COCH₂—O— | 96 ± 25 | >1000 (30% inhibition) | >10 | N—[8-(4'-carboxymethyloxyphenyl)-1,3-dipropyl-xanthine]dicyclohexylurea |
| 5 | succinimide-N—OCOCH₂—O— | 9.0 ± 0.7 | 30 | 3.3 | 8-(4'-carboxymethyloxyphenyl)-1,3-dipropyl-xanthine n-hydroxysuccinimide ester |
| 6a | H₂NCOCH₂—O— | 6.0 ± 1.0 | 47 ± 2 | 7.8 | 8-(4'-carboxymethyloxyphenyl)-1,3-dipropyl-xanthine carboxamide |
| 6b | (CH₃)₂CHNHCOCH₂—O— | Not tested | | | 8-(4'-carboxymethyloxyphenyl)-1,3-dipropyl- |

TABLE 1-continued

| Compound | 8-Phenyl Substituent | $K_i$(nM) A₁-Receptor | $K_i$(nM) A₂-Receptor | A₂/A₁ Ratio | Name |
|---|---|---|---|---|---|
| 6c | (CH₃)₂NCOCH₂—O— | 32 ± 7 | 68 ± 39 | 2.1 | xanthine isopropylamide 8-(4'-carboxymethyloxyphenyl)-1,3-dipropyl-xanthine dimethylamide |
| 6d | H₂N—(CH₂)₂NHCOCH₂—O— | 1.2 ± 0.5 | 49 ± 17 | 41.0 | 8-(4'-carboxymethyloxyphenyl)-1,3-dipropyl-xanthine-2-aminoethylamide |
| 6e | H₂N—(CH₂)₈NHCOCH₂—O— | 5 | 470 | 94 | 8-(4'-carboxymethyloxyphenyl)-1,3-dipropyl-xanthine-8-amino-octylamide |
| 6f | [structure: 4-OH, 3-NHCOCH₂—O—, 4-(N-Et·SO₃H morpholine) phenyl] | 150 | 150 | 1.0 | 8-(4'-carboxymethyloxyphenyl)-1,3-dipropyl-xanthine-o-hydroxy-m-sulfoanilide N—ethylmorpholine salt |
| 6g | H₂N—NHCOCH₂—O— | 59 ± 0.7 | 32 | 0.54 | 8-(4'-carboxymethyloxyphenyl)-1,3-dipropyl-xanthine hydrazide |
| 7a | CH₃CONH—(CH₂)₂—NHCOCH₂—O— | 24 ± 3.5 | 62 ± 3 | 2.6 | 8-(4'-carboxymethyloxyphenyl)-1,3-dipropyl-xanthine 2-(acetylamino)-ethylamide |
| 7b | BrCH₂CONH(CH₂)₂—NHCOCH₂—O— | 33 | | | 8-(4'-carboxymethyloxyphenyl)-1,3-dipropyl-xanthine 2-(bromoacetylamino)-ethylamide |
| 7c | [thienyl]—CH₂CONH—(CH₂)₂—NHCOCH₂—O— | 9 | | | 8-(4'-carboxymethyloxyphenyl)-1,3-dipropyl-xanthine 2-(2'-thienylacetylamino)-ethylamide |
| 7d | Biotinyl NH(CH₂)₂—NHCOCH₂—O— | 54 ± 2 | 180 ± 80 | 3.3 | 8-(4'-carboxymethyloxyphenyl)-1,3-dipropyl-xanthine 2-(biotinylamino)-ethylamide |
| 7e | [biotin]—(CH₂)₄CONH(CH₂)₅CO—NHCOCH₂— | 52 | | | 8-(4'-carboxymethyloxyphenyl)-1,3-dipropyl-xanthine 2-(biotinyl-ε-aminocapropylamino)-ethylamide |
| 8a | [4-HO-phenyl]-CH₂—Y | not tested | | | 8-(4'-carboxymethyloxyphenyl)-1,3-dipropyl-xanthine-2(N—(4-hydroxy)benzylamino)-ethylamide |

TABLE 1-continued

| Compound | 8-Phenyl Substituent | $K_i$ (nM) $A_1$-Receptor | $K_i$ (nM) $A_2$-Receptor | $A_2/A_1$ Ratio | Name |
|---|---|---|---|---|---|
| 8b | HO—⟨phenyl⟩—CH$_2$N(CH$_2$)$_2$NHCOCH$_2$—CH$_2$CH$_3$·HOAc | 2.2 ± 0.7 | 320 ± 70 | 145 | 8-(4'-carboxymethyloxyphenyl)-1,3-dipropyl-xanthine-2(N—4-hydroxybenzyl-ethylamino)-ethylamide acetate |
| 8c | HO—⟨phenyl-F⟩—CH$_2$—NH—(CH$_2$)$_2$—NHCOCH$_2$ | Not tested | | | 8-(4'-carboxymethyloxyphenyl)-1,3-dipropyl-xanthine-2(N—(3-fluoro-4-hydroxybenzyl-amino)-ethylamide |
| 9 | CH$_3$<br>HOOC—(CH$_2$)$_4$—CH—Y | Not tested | | | 6-[N—(8-(4'-carboxymethyloxyphenyl)-1,3-dipropyl-xanthine-2-ethylamide]-n-heptanoic acid |
| 10 | (HO$_2$C—CH$_2$—)$_2$N—(CH$_2$)$_2$—N(CH$_2$COOH)—(CH$_2$)$_2$—N(CH$_2$COOH)—CH$_2$CO—Y— | 260 | 130 | 0.5 | 8-(4'-carboxymethyl(oxyphenyl)-1,3-dipropyl-xanthine-2-(N,N—(bis[carboxymethyl]amino)-ethyl]glycylamino)ethylamide |

*1,3-Dimethylxanthine; all others are 1,3-dipropyl- $$Y = -NH-(CH_2)_2-NH-\overset{\overset{O}{\|}}{C}-CH_2-O$$

biotinyl = 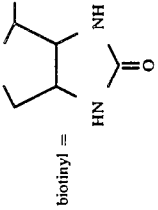

TABLE 1-A

All amino acids are of the L-configuration unless noted

| Compound | 8-Phenyl Substituent | $K_i$ (nM) $A_1$-Receptor | $K_i$ (nM) $A_2$-Receptor | $A_2/A_1$ Ratio | Name |
|---|---|---|---|---|---|
| 11 | HN—C(=NH)—Y— | 0.9 | n.t. | — | 8-(4'-carboxymethyloxyphenyl)-1,3-dipropyl-xanthine-2-guanidinoethylamide |
| 12a | —O—CH₂—C(O)—Gly—OBu$^t$ | 11 | 50 | 4.5 | 1,3-dipropylxanthine-8-(4-phenyloxyacetyl)-glycine-t-butyl ester |
| 12b | —O—CH₂—C(O)—Gly—OH | 60 | 70 | 1.2 | 1,3-dipropylxanthine-8-(4-phenyloxyacetyl)-glycine |
| 13a | —O—CH₂—C(O)—Lys(Cbz)—OBu$^t$ | 19 | 120 | 6.3 | 1,3-dipropylxanthine-8-(4-phenyloxyacetyl)-(N—carbobenzyloxy)-L-lysine t-butyl ester |
| 13b | —O—CH₂—C(O)—Lys(H)—OH | 20 | 70 | 3.5 | 1,3-dipropylxanthine-8-(4-phenyloxyacetyl)-N—lysine |
| 14a | Cbz—Gly—Y— | 5 | 50 | 10 | 8-(4'-carboxymethyloxyphenyl)-1,3-dipropyl-xanthine-2-(N—benzyloxycarbonyl-glycyl-amino)-ethylamide |
| 14b | HBr.H—Gly—Y— | 2.3 | 70 | 30 | 8-(4'-carboxymethyloxyphenyl)-1,3-dipropyl-xanthine-2-(glycyl-amino)-ethylamide |
| 15a | Cbz—(Gly)₂—Y— | 0.95 | 80 | 84 | 8-(4'-carboxymethyloxyphenyl)-1,3-dipropyl-xanthine-2-(N—benzyloxycarbonyl-glycyl-glycyl-amino)-ethylamide |
| 15b | HBr.H—(Gly)₂—Y— | 1.5 | 80 | 53 | 8-(4'-carboxymethyloxyphenyl)-1,3-dipropyl-xanthine-2-(glycyl-glycyl-amino)-ethylamide |
| 15c | biotinyl-(Gly)₂—Y— | 60 | 120 | 2.0 | 8-(4'-carboxymethyloxyphenyl)-1,3-dipropyl-xanthine-2-(biotinyl-glycyl-glycyl-amino)-ethylamide |
| 16a | Cbz—Asn—Y— | 4.5 | 80 | 18 | 8-(4'-carboxymethyloxyphenyl)-1,3-dipropyl-xanthine-2-(N—benzyloxycarbonyl-L-asparaginyl-amino)-ethylamide |
| 16b | HBr.H—Asn—Y— | 7.0 | 70 | 10 | 8-(4'-carboxymethyloxyphenyl)-1,3-dipropyl-xanthine-2-(L-asparaginyl-amino)-ethylamide |
| 17a | Boc—Gln—Y— | 10 ± 1.1 | 80 | 4.0 | 8-(4'-carboxymethyloxyphenyl)-1,3-dipropyl-xanthine-2-(N—t-butyloxycarbonyl-L-glutaminyl-amino)-ethylamide |
| 17b | TFA.H—Gln—Y— | 19 ± 2.1 | 100 | 5.3 | 8-(4'-carboxymethyloxyphenyl)-1,3-dipropyl-xanthine-2-(L-glutaminyl-amino)-ethylamide |
| 18a | Boc—Leu—Y— | 29 | 100 | 3.4 | 8-(4'-carboxymethyloxyphenyl)-1,3-dipropyl-xanthine-2-(N—t-butyloxycarbonyl-L-leucyl-amino)-ethylamide |
| 18b | TFA.H—Leu—Y— | 1.8 | 80 | 44 | 8-(4'-carboxymethyloxyphenyl)-1,3-dipropyl-xanthine-2-(L-leucyl-amino)-ethylamide |
| 19a | Boc—Met—Y— | 18 | 110 | 6.1 | 8-(4'-carboxymethyloxyphenyl)-1,3-dipropyl-xanthine-2-(N—t-butyloxycarbonyl-L-methionyl-amino)-ethylamide |
| 19b | TFA.H—Met—Y— | 1.3 | 90 | 69 | 8-(4'-carboxymethyloxyphenyl)-1,3-dipropyl-xanthine-2-(L-methionyl-amino)-ethylamide |
| 20a | Boc—Lys(Cbz)—Y— | (9.3) | 50 | 5.4 | 8-(4'-carboxymethyloxyphenyl)-1,3-dipropyl-xanthine-2-(N—t-butyloxycarbonyl- -benzyloxy-carbonyl-L-lysyl-amino)-ethylamide |
| 20b | (HBr)₂.H—Lys(H)—Y— | 1.8 + 0.4 | 20 | 11 | 8-(4'-carboxymethyloxyphenyl)-1,3-dipropyl-xanthine-2-(L-lysyl-amino)-ethylamide |
| 21a | Boc—D-Lys(Cbz)—Y— | (11) | 100 | 9 | 8-(4'-carboxymethyloxyphenyl)-1,3-dipropyl-xanthine-2-(N—t-butyloxycarbonyl- -benzyloxycarbonyl-D-lysyl-amino)-ethylamide |
| 21b | Boc—D-Lys(H)—Y— | 5.2 | n.t. | — | 8-(4'-carboxymethyloxyphenyl)-1,3-dipropyl-xanthine-2-(N—t-butyloxycarbonyl-D-lysyl-amino)-ethylamide |
| 21c | TFA.H—D-Lys(Cbz)—Y— | n.t. | — | — | 8-(4'-carboxymethyloxyphenyl)-1,3-dipropyl-xanthine-2-( -benzyloxycarbonyl-D-lysyl-amino)-ethylamide |
| 21d | (HBr)₂.H—D-Lys(H)—Y— | 1.0 | 20 | 20 | 8-(4'-carboxymethyloxyphenyl)-1,3-dipropyl-xanthine-2-(D-lysyl-amino)-ethylamide |
| 22a | Boc—D-Lys—Y—, with side chain CO—C₆H₄—CH₂Br | 67 | n.t. | — | 8-(4'-carboxymethyloxyphenyl)-1,3-dipropyl-xanthine-2-(N—t-butyloxycarbonyl- -4-bromo-methylbenzoylacetyl—D-lysyl-amino)-ethylamide |

TABLE 1-A-continued

All amino acids are of the L-configuration unless noted

| Compound | 8-Phenyl Substituent | $K_i$ (nM) $A_1$-Receptor | $K_i$ (nM) $A_2$-Receptor | $A_2/A_1$ Ratio | Name |
|---|---|---|---|---|---|
| 22b | TFA.H—D-Lys—Y— CO—C6H4—CH2Br | 6.5 | n.t. | — | 8-(4'-carboxymethyloxyphenyl)-1,3-dipropyl-xanthine-2-( -4-bromomethylbenzoylacetyl-D-lysyl-amino)-ethylamide |
| 23a | Boc—D-Lys—Y— CO(CH2)2—C6H4—OH | 20 | n.t. | — | 8-(4'-carboxymethyloxyphenyl)-1,3-dipropyl-xanthine-2-(N—t-butyloxycarbonyl- -4-hydroxy-phenylpropionyl-D-lysyl-amino)-ethylamide |
| 23b | TFA—D-Lys—Y— CO(CH2)2—C6H4—OH | 1.9 | n.t. | — | 8-(4'-carboxymethyloxyphenyl)-1,3-dipropyl-xanthine-2-( -4-hydroxyphenylpropionyl-D-lysyl-amino)-ethylamide |
| 24a | Boc—Cit—Y— | 52 | 80 | 1.5 | 8-(4'-carboxymethyloxyphenyl)-1,3-dipropyl-xanthine-2-(N—t-butyloxycarbonyl-L-citrullyl-amino)-ethylamide |
| 24b | TFA.H—Cit—Y— | 2.8 | 70 | 25 | 8-(4'-carboxymethyloxyphenyl)-1,3-dipropyl-xanthine-2-(L-citrullyl-amino)-ethylamide |
| 25a | Boc—Phe—Y— | 32 | 130 | 4.1 | 8-(4'-carboxymethyloxyphenyl)-1,3-dipropyl-xanthine-2-(N—t-butyloxycarbonyl-L-phenyl-alanyl-amino)-ethylamide |
| 25b | TFA.H—Phe—Y— | 1.8 | 100 | 56 | 8-(4'-carboxymethyloxyphenyl)-1,3-dipropyl-xanthine-2-(L-phenylalanyl-amino)-ethylamide |
| 26a | Cbz—L-Tyr—Y— | 22 | 120 | 5.5 | 8-(4'-carboxymethyloxyphenyl)-1,3-dipropyl-xanthine-2-(N—benzyloxycarbonyl-L-tyrosyl-amino)-ethylamide |
| 26b | HBr.H—L-Tyr—Y— | 2.0 | 100 | 50 | 8-(4'-carboxymethyloxyphenyl)-1,3-dipropyl-xanthine-2-(L-tyrosyl-amino)-ethylamide |
| 27a | Boc—Tyr(3-iodo)-Y— | 119 | n.t. | — | 8-(4'-carboxymethyloxyphenyl)-1,3-dipropyl-xanthine-2-(N—t-butyloxycarbonyl-3-iodo-L-tyrosyl-amino)-ethylamide |
| 27b | TFA.H—Tyr(3-iodo)-Y— | 4.7 | n.t. | — | 8-(4'-carboxymethyloxyphenyl)-1,3-dipropyl-xanthine-2-(3-iodo-L-tyrosyl-amino)-ethylamide |
| 28a | Boc—D-Tyr—Y— | 46 ± 2.0 | n.t. | — | 8-(4'-carboxymethyloxyphenyl)-1,3-dipropyl-xanthine-2-(N—t-butyloxycarbonyl-D-tyrosyl-amino)-ethylamide |
| 28b | TFA.H—D-Tyr—Y— | 5.3 ± 0.48 | n.t. | — | 8-(4'-carboxymethyloxyphenyl)-1,3-dipropyl-xanthine-2-(D-tyrosyl-amino)-ethylamide |
| 29a | Boc—D-Tyr—D-Lys(Cbz)—Y— | 56 | n.t. | — | 8-(4'-carboxymethyloxyphenyl)-1,3-dipropyl-xanthine-2-(N—t-butyloxycarbonyl-D-tyrosyl-benzyloxycarbonyl-D-lysyl-amino)-ethylamide |
| 29b | (HBr)2.H—D-Tyr—D-Lys(H)—Y— | 1.8 | n.t. | — | 8-(4'-carboxymethyloxyphenyl)-1,3-dipropyl-xanthine-2-(D-tyrosyl-D-lysyl-amino)-ethylamide |
| 30a | Boc—Trp—Y— | 65 | 130 | 2.0 | 8-(4'-carboxymethyloxyphenyl)-1,3-dipropyl-xanthine-2-(N—t-butyloxycarbonyl-L-tryptophanyl-amino)-ethylamide |
| 30b | TFA.H—Trp—Y— | 5.0 | 100 | 20 | 8-(4'-carboxymethyloxyphenyl)-1,3-dipropyl-xanthine-2-(L-tryptophanyl-amino)-ethylamide |
| 31a | Boc—Tha—Y— | 17 ± 1.65 | n.t. | — | 8-(4'-carboxymethyloxyphenyl)-1,3-dipropyl-xanthine-2-(N—t-butyloxycarbonyl-3(2'-thienyl)-L-alanyl-amino)-ethylamide |
| 31b | TFA.H—Tha—Y— | 1.3 ± 0.12 | 130 | 100 | 8-(4'-carboxymethyloxyphenyl)-1,3-dipropyl-xanthine-2-(3(2'-thienyl)-L-alanyl-amino)-ethylamide |

TABLE 2

| Compound | 8-Phenyl Substituent** | Solubility* |
|---|---|---|
| — | HO— | 3.2 micromolar |
| 1b | HO2C—CH2—O— | 1.2 millimolar |
| 6a | H2NCOCH2—O— | 26 micromolar |
| 6d | H2N—(CH2)2NHCOCH2—O— | 90 micromolar (primary amine with 2 methylenes) |
| 6g | H2N—NHCOCH2—O— | 36 micromolar |
| 7a | CH3CONH—(CH2)2—NHCOCH2—O— | 8.6 micromolar |
| 9 | HOOC—(CH2)4CH—NH— (CH3) (CH2)2NHCOCH2O— | 110 micromolar |
| 21d | HBr.H—D-Lys(H)—Y— | 340 micromolar |
| 24b | TFA.H—Cit—Y— | 250 micromolar |

TABLE 2-continued

| Compound | 8-Phenyl Substituent** | Solubility* |
|---|---|---|
| 26b | H₂N—CH—CONH—(CH₂)₂—<br>　　　｜　　　NHCOCH₂—O—<br>　　　CH₂<br>　　　｜<br>　　(C₆H₄)<br>　　　｜<br>　　OH | 36 micromolar |

*pH 7.2, 0.1 M sodium phosphate
**All compounds are 1,3-dipropyl derivatives
A value of 20 micromolar for solubility is deemed superior with reference to this table.

TABLE 3

| Compound | Synthetic Method | Yield (%) |
|---|---|---|
| 12a | A | 56 |
| 12b | E | 78 |
| 13a | A | 85 |
| 13b | D | 100 |
| 14a | B | 36 |
| 14b | D | 93 |
| 15a | B | 69 |
| 15b | D | 55 |
| 15c | C | 85 |
| 16a | B | 92 |
| 16b | D | 76 |
| 17a | C | 48 |
| 17b | E | |
| 18a | C | 82 |
| 18b | E | 98 |
| 19a | C | 47 |
| 19b | E | 73 |
| 20a | C | 39 |
| 20b | D | 100 |
| 21a | | |
| 21b | F | 54 |
| 21c | E | 100 |
| 21d | D | 100 |
| 22a | A | 82 |
| 22b | E | 62 |
| 23a | C | 17 |
| 23b | E | 93 |
| 24a | B | 71 |
| 24b | E | 68 |
| 25a | C | 63 |
| 25b | E | 100 |
| 26a | B | 89 |
| 26b | D | 81 |
| 27a | C | 41 |
| 27b | E | 100 |
| 28a | C | 70 |
| 28b | E | 88 |
| 30a | C | 70 |
| 30b | E | 93 |
| 31a | C | 71 |
| 31b | E | 98 |

A = carbodiimide coupling
B = p-nitrophenyl ester coupling to compound 2d
C = N—hydroxysuccinimide ester coupling
D = HBr/HOAc
E = TFA
F = H₂/Pd

TABLE 4

Partition Coefficients of Xanthine Amino Acid Conjugates
(free α-amino conjugates unless specified)

| Compound | Amino Acid | log (Conc. in octanol phase / Conc. in aqueous phase) |
|---|---|---|
| 28b | D-Tyr | 2.0 |
| 32b | Tha | 2.0 |
| 13b | Lys* | 0.29 |
| 18b | Leu | 1.9 |
| 14b | Gly | 1.4 |
| 15b | Gly—Gly | 1.0 |

TABLE 4-continued

Partition Coefficients of Xanthine Amino Acid Conjugates
(free α-amino conjugates unless specified)

| Compound | Amino Acid | log (Conc. in octanol phase / Conc. in aqueous phase) |
|---|---|---|
| 24b | Cit | 0.81 |

*Free α-carboxylate

We claim:

1. Compounds having the formula:

A—B where
A and B are linked together in an amide linkage, and
where A (the primary pharmacophore) is:

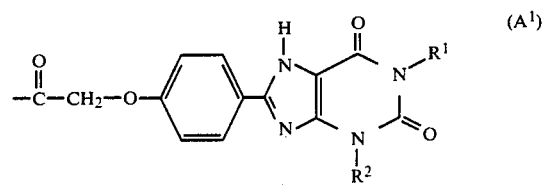

(A¹)

or

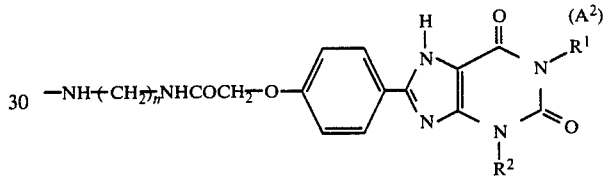

(A²)

where
$R^1$ and $R^2$ are alkyl of 1–6 carbons and n=2–6
and B (the carrier) is a natural amino acid of the L or D configuration or an oligopeptide having 2–5 natural amino acids of the L or D configuration, or an oligopeptide having 1–5 natural amino acids of the L or D configuration in which a 3(2'-thienyl) alanine moiety is bonded through an amide linkage to the terminal amino acid of said oligopeptide, or a 3(2'-thienyl) alanine moiety.

2. The compound of claim 1 having the name 8-(4'-carboxymethyloxyphenyl)-1,3-dipropyl xanthine 2-(glycyl-glycyl-amino)-ethylamide.

3. The compound of claim 1 having the name 8-(4'carboxymethyloxyphenyl)-1,3-dipropyl xanthine 2-(L-methionyl-amino)-ethylamide.

4. The compound of claim 1 having the name 8-(4'-carboxymethyloxyphenyl)-1,3-dipropyl xanthine 2-(L-lysyl-amino)-ethylamide.

5. The compound of claim 1 having the name 8-(4'-carboxymethyloxyphenyl)-1,3-dipropyl xanthine 2-(D-lysyl-amino)-ethylamide.

6. The compound of claim 1 having the name 8-(4'-carboxymethyloxyphenyl)-1,3-dipropyl xanthine 2-(L-citrullyl-amino)-ethylamide.

7. The compound of claim 1 having the name 8-(4'-carboxymethyloxyphenyl)-1,3-dipropyl xanthine 2-(L-tyrosyl-amino)-ethylamide.

8. The compound of claim 1 having the name 8-(4'-carboxymethyloxyphenyl)-1,3-dipropyl xanthine 2-(D-tyrosyl-D-lysyl-amino)-ethylamide.

9. The compound of claim 1 having the name 8-(4'-carboxymethyloxyphenyl)-1,3-dipropyl xanthine 2-(3(2'-thienyl)-L-alanyl-amino)-ethylamide.

10. The compound of claim 1 having the name 8-(4'-carboxymethyloxyphenyl)-1,3-dipropylxanthine-2-(L-leucyl-amino)-ethylamide.

11. The compound of claim 1 having the name 8-(4'-carboxymethyloxyphenyl)-1,3-dipropylxanthine-2-(L-phenylalanyl-amino)-ethylamide.

12. A pharmaceutical composition useful as hypotensive/vasodilator and antithrombotic reagents comprising a compound as defined in claim 1 and the pharmaceutically acceptable salts thereof in combination with a pharmaceutically acceptable carrier.

13. The compound having the name 8-(4'-carboxymethyloxyphenyl)-1,3-dipropyl xanthine 2-(E-4-hydroxyphenylpropionyl-D-lysyl-amino)-ethylamide.

* * * * *